United States Patent
Hill et al.

(10) Patent No.: US 7,759,064 B2
(45) Date of Patent: Jul. 20, 2010

(54) DEVELOPMENT OF PCR PRIMERS AND PRIMER MIXTURES FOR AMPLIFICATION OF CNP60 TARGET SEQUENCES

(76) Inventors: Janet Elizabeth Hill, 802 10th St. E. Saskatoon, Saskatchewan S7H 0H3 (CA); Jennifer Rae Town, #118, 515 McWillie Ave, Saskatoon, SK (CA) S7S 1K8; Sean Mathias Hemmingsen, Site 502, Box 29, RRS, Saskatoon SK (CA) S7K 3J8

(*) Notice: Subject to any disclaimer, the term of this patent is extended or adjusted under 35 U.S.C. 154(b) by 0 days.

(21) Appl. No.: 11/997,655

(22) PCT Filed: Aug. 1, 2006

(86) PCT No.: PCT/CA2006/001278

§ 371 (c)(1),
(2), (4) Date: Feb. 1, 2008

(87) PCT Pub. No.: WO2007/014468

PCT Pub. Date: Feb. 8, 2007

(65) Prior Publication Data

US 2008/0311629 A1    Dec. 18, 2008

Related U.S. Application Data

(60) Provisional application No. 60/703,896, filed on Aug. 1, 2005.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/22.1; 536/24.33

(58) Field of Classification Search ............... 435/6, 435/91.2; 536/22.1, 24.33
See application file for complete search history.

(56) References Cited

U.S. PATENT DOCUMENTS 5,708,160 A * 1/1998 Goh et al. ............. 536/24.32

FOREIGN PATENT DOCUMENTS

WO        03052141      * 6/2003

OTHER PUBLICATIONS

Hill, J.E. et al "Improved template representation in cpn60 polymerase chain reation (PCR) product libraries generated from complex templates by application of specific mixture of PCR primers" Environmental Microbiology Apr. 2006 vol. 8 No. 4 pp. 741-746 ISSN 1462-2913.

Goh, S.H. et al "HSP60 gene sequences as universal targets for microbial species identification: Studies with coagulase-negative *Staphylococci*" Journal of Clinical Microbiology Apr. 1996 vol. 34 No. 4 pp. 818-823 ISSN 0095-1137.

Hill, J.E. et al "Extneisve profiling of a complex microbial community by highthroughput seuqencing" Applied and Environmental Microbiology Jun. 2002 vol. 68 No. 6 pp. 3055-3066 ISSN 0099-2240.

* cited by examiner

*Primary Examiner*—Kenneth R. Horlick
*Assistant Examiner*—Joyce Tung
(74) *Attorney, Agent, or Firm*—Michael R. Williams; Ade & Co Inc.

(57) ABSTRACT

We have developed the primer pair H1511 and H1261 as a replacement for primer pair H279/H280 for specific amplification of cpn60 universal target sequences in genomic DNA or in complex DNA mixtures, including those with high G+C content.

6 Claims, 3 Drawing Sheets

SEQUENCE LISTING

```
<160> NUMBER OF SEQ ID NOS: 6

<210> SEQ ID NO 1
<211> LENGTH: 26
<212> TYPE: DNA
<213> ORGANISM: artificial
<220> FEATURE:
<223> OTHER INFORMATION: cpn60 universal primer

<400> SEQUENCE: 1
gacgtcgccg gtgacggcac caccac                                          26

<210> SEQ ID NO 2
<211> LENGTH: 26
<212> TYPE: DNA
<213> ORGANISM: artificial
<220> FEATURE:
<223> OTHER INFORMATION: cpn60 primer

<400> SEQUENCE: 2
cgacggtcgc cgaagcccgg ggcctt                                          26

<210> SEQ ID NO 3
<211> LENGTH: 50
<212> TYPE: DNA
<213> ORGANISM: artificial
<220> FEATURE:
<223> OTHER INFORMATION: cpn60 primer with M1340F sequencing primer

<400> SEQUENCE: 3
cgccagggtt ttcccagtca cgacgacgtc gccggtgacg gcaccaccac                50

<210> SEQ ID NO 4
```

-continued

```
<211> LENGTH: 50
<212> TYPE: DNA
<213> ORGANISM: artificial
<220> FEATURE:
<223> OTHER INFORMATION: cpn60 primer with M1348R sequencing primer

<400> SEQUENCE: 4
agcggataac aatttcacac aggacgacgg tcgccgaagc ccggggcctt          50

<210> SEQ ID NO 5
<211> LENGTH: 24
<212> TYPE: DNA
<213> ORGANISM: artificial
<220> FEATURE:
<223> OTHER INFORMATION: cpn60 primer

<400> SEQUENCE: 5
cgccagggtt ttcccagtca cgac                                     24

<210> SEQ ID NO 6
<211> LENGTH: 24
<212> TYPE: DNA
<213> ORGANISM: artificial
<220> FEATURE:
<223> OTHER INFORMATION: cpn60 primer

<400> SEQUENCE: 6
agcggataac aatttcacac agga                                     24
```

DEVELOPMENT OF PCR PRIMERS AND PRIMER MIXTURES FOR AMPLIFICATION OF CNP60 TARGET SEQUENCES

PRIOR APPLICATION INFORMATION

This application claims the benefit of U.S. Provisional Patent Application 60/703,896, filed Aug. 1, 2005.

BACKGROUND OF THE INVENTION

The invention relates to the development of PCR primers and primer mixtures.

In our experience with PCR amplification of cpn60 universal target sequences from genomic DNA templates from individual organisms, we have found that templates containing at least 57% G+C are problematic and are usually difficult or impossible to amplify with conventional primers H279/H280 or H729/H730 (the so-called cpn60"universal primers" or "inosine primers" or "I primers"). Chaperonin-60(cpn60) proteins are sequence-related molecular chaperones found in prokaryotes and in the plastids and mitochondria of eukaryotes.

High G+C content organisms include organisms of significance to agriculture, human and animal health, industry and the environment. They are important members of microbial communities. Given the status quo, the inability to amplify partial cpn60 sequences from these types of organisms makes them inaccessible to present methods, preventing the development of methods to detect and identify them or to take stock of them in complex microbial communities.

More specifically, the problems are that inosine is not a "neutral" base, inosine-based primers bind less efficiently with increasing G+C content and such primers fail to amplify from templates with G+C content of greater than 58% in the cpn60 universal target region.

SUMMARY OF THE INVENTION

According to one aspect of the invention, we have developed the primer pair H1511 and H1261 as a replacement for primer pair H279/H280 for specific amplification of cpn60 universal target sequences in genomic DNA or in complex DNA mixtures, including those with high G+C content.

According to another aspect of the invention, we have developed the primer pair H1594/H1595 for amplification of cpn60 targets having high G+C content.

According to yet another aspect of the invention, we have developed a cocktail of primer pairs H1594/H1595 and H729/H730 in various ratios for universal target amplification.

According to another aspect of the invention, there is provided a primer pair for amplification of cpn60 targets having high G+C content comprising:

a first primer comprising a nucleotide sequence as set forth in SEQ ID NO. 1; and a second primer comprising a nucleotide sequence as set forth in SEQ ID NO. 2.

According to a further aspect of the invention, there is provided a method of amplifying partial cpn60 sequences from genomic DNA comprising:

a) providing a sample comprising at least one bacterial target;

b) adding a primer pair for amplification of cpn60 targets having high G+C content comprising:

a first primer comprising a nucleotide sequence as set forth in SEQ ID NO. 1; and a second primer comprising a nucleotide sequence as set forth in SEQ ID NO. 2; and c) incubating the sample under conditions suitable for nucleotide amplification.

DETAILED DESCRIPTION OF THE INVENTION

Figure 1:
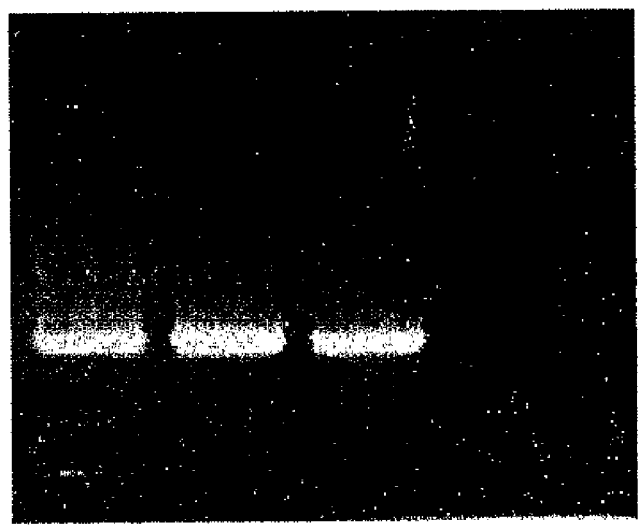
FIG. 1. PCR amplification of cpn60 sequences from individual high G+C templates. Templates are *Arthrobacter* sp. awr183 (j0438, environmental isolate, 60% G+C), *Pseudomonas* sp. MF Q E 2-40 (j0495, environmental isolate, 59% G+C) and *Stenotrophomonas* sp. MF Q E 3-39 (j0508, environmental isolate, 63% G+C). N=no template (negative control). None of these templates were amplifiable with the inosine-based primers.

As used herein, "purified" does not require absolute purity but is instead intended as a relative definition. For example, purification of starting material or natural material to at least one order of magnitude, preferably two or three orders of magnitude is expressly contemplated as falling within the definition of "purified".

As used herein, the term "isolated" requires that the material be removed from its original environment.

In the context of this invention, primer pair means a pair of oligonucleotide primers which are employed in the amplification process, which is an enzymatic chain reaction that produces exponential quantities of polymorphic locus relative to the number of reaction steps involved. Typically, one primer is complementary to the negative (−) strand of the polymorphic locus and the other primer is complementary to the positive (+) strand.

Primer H1511 was originally designed as one of a pair of primers for amplification of *Bifidobacterium* cpn60 sequences. Primer 1261 was originally designed as one of a pair of primers for amplification of cpn60 sequences from *Bordetella* spp. derived from clinical specimens. As a pair, our lab refers to these as the "magic primers" or "M primers".

---

The non-degenerate magic primers based on *Bifidobacterium* (forward) and *Bordetella* (reverse).

H1511
(SEQ ID No. 1)
5'-GAC GTC GCC GGT GAC GGC ACC ACC AC-3'

H1261
(SEQ ID No. 2)
5'-CGA CGG TCG CCG AAG CCC GGG GCC TT-3'

-continued

The non-degenerate magic primers based on
Bifidobacterium (forward) and Bordetella
(reverse).

H1594 (M1340F sequencing primer underlined)
(SEQ ID No. 3)
5'-<u>CGC CAG GGT TTT CCC AGT CAC GAC</u> GAC GTC GCC GGT
GAC GGC ACC ACC AC-3'

H1595 (M1348R sequencing primer underlined)
(SEQ ID No. 4)
5'-<u>AGC GGA TAA CAA TTT CAC ACA GGA</u> CGA CGG TCG CCG
AAG CCC GGG GCC TT-3'

H729
(SEQ ID No. 5)
5'-CGCCAGGGTTTTCCCAGTCACGAC-H279-3'

H730
(SEQ ID No. 6)
5'-AGCGGATAACAATTTCACACAGGA-H280-3'

As will be apparent to one of skill in the art, the sequences underlined above were added to these primers in order to facilitate the direct sequence determination of amplified sequences without the need for a cloning step. This saves time and money but is not necessarily an essential feature of the invention.

Described herein is a primer pair for amplification of cpn60 targets having high G+C content comprising: a first primer comprising a nucleotide sequence as set forth in SEQ ID NO. 1; and a second primer comprising a nucleotide sequence as set forth in SEQ ID NO. 2. In other embodiments, the first primer may consist essentially of a nucleotide sequence as set forth in SEQ ID NO. 1; and the second primer may consist essentially of a nucleotide sequence as set forth in SEQ ID NO. 2. In yet other embodiments, the first primer may consist of a nucleotide sequence as set forth in SEQ ID NO. 1; and the second primer may consist of a nucleotide sequence as set forth in SEQ ID NO. 2.

Described herein is a primer pair for amplification of cpn60 targets having high G+C content comprising: a first primer comprising a nucleotide sequence as set forth in SEQ ID NO. 3; and a second primer comprising a nucleotide sequence as set forth in SEQ ID NO. 4. In other embodiments, the first primer may consist essentially of a nucleotide sequence as set forth in SEQ ID NO. 3; and the second primer may consist essentially of a nucleotide sequence as set forth in SEQ ID NO. 4. In yet other embodiments, the first primer may consist of a nucleotide sequence as set forth in SEQ ID NO. 3; and the second primer may consist of a nucleotide sequence as set forth in SEQ ID NO. 4. As discussed above, SEQ ID No. 3 corresponds to SEQ ID No. 1 and an M13(40)F standard sequencing primer whereas SEQ ID No. 4 corresponds to SEQ ID No. 2 and an M13 (−48)R standard sequencing primer. Accordingly, these primers are suitable for situations wherein it is useful to obtain the sequence of an amplified cpn60 sequence without the need for a cloning step.

In some embodiments, the target has a high G+C content, that is, for example, a G+C content at the target region to be amplified for example the in the cpn60 universal target region that exceeds 58%.

In another aspect of the invention, the above-described primers are used in a method of amplifying partial cpn60 sequences from genomic DNA comprising:

a) providing a sample comprising at least one bacterial target;
b) adding a primer pair for amplification of cpn60 targets having high G+C content comprising:
a first primer comprising a nucleotide sequence as set forth in SEQ ID NO. 1; and
a second primer comprising a nucleotide sequence as set forth in SEQ ID NO. 2; and
c) incubating the sample under conditions suitable for nucleotide amplification.

Examples of conditions suitable for nucleotide amplification are well-known to those of skill in the art and include enzymes, buffers, nucleotides, incubation times and temperatures and the like. Exemplary PCR conditions will be readily apparent to one of skill in the art.

In other embodiments, the primers may consist essentially of or may consist of a nucleotide sequence as set forth is SEQ ID Nos. 1 or 2 as discussed above.

As discussed above, the primers as set forth in SEQ ID No. 3 and SEQ ID No. 4 may be substituted for the primers as set forth in SEQ ID No. 1 and SEQ ID No. 2 respectively.

In some embodiments, a second primer pair comprising a third primer comprising a nucleotide sequence as set forth in SEQ ID NO. 5 and a fourth primer comprising a nucleotide sequence as set forth in SEQ ID NO. 6 are added to the mixture prior to step (c). The third primer may consist essentially of a nucleotide sequence as set forth in SEQ ID NO. 5 and the fourth primer may consist essentially of a nucleotide sequence as set forth in SEQ ID NO. 6. In other embodiments, the third primer may consist of a nucleotide sequence as set forth in SEQ ID NO. 5 and the fourth primer may consist of a nucleotide sequence as set forth in SEQ ID NO. 6.

As will be appreciated by one of skill in the art, as used herein, 'first primer', 'second primer', 'third primer' and 'fourth primer' are relative terms and serve to identify the primers but do not indicate a required order of addition.

As discussed below, the first primer pair and the second primer pair may be added to the sample at a concentration at a ratio of from 1:1 to 10:1 compared to the concentration of the third primer and the fourth primer in the sample. Specifically, the ratio may be from 1:1 to 10:1 or from 1:1 to 9:1 or from 1:1 to 8:1 or from 1:1 to 7:1 or from 1:1 to 6:1 or from 1:1 to 5:1 or from 1:1 to 4:1 or from 1:1 to 3:1 or from 1:1 to 2:1. This mixture comprising two primer pairs can be used for amplification of partial cpn60 sequences from organisms of both high and low G+C content as discussed below.

Application of H1511/H1261 alone—generation of PCR products from individual high G+C template DNAs.

Primers H1511/H1261 has been applied to numerous template DNAs for the PCR amplification of cpn60 sequences. As an example, FIG. 1 shows the amplification products from 3 individual template DNAs.

Figure 2:
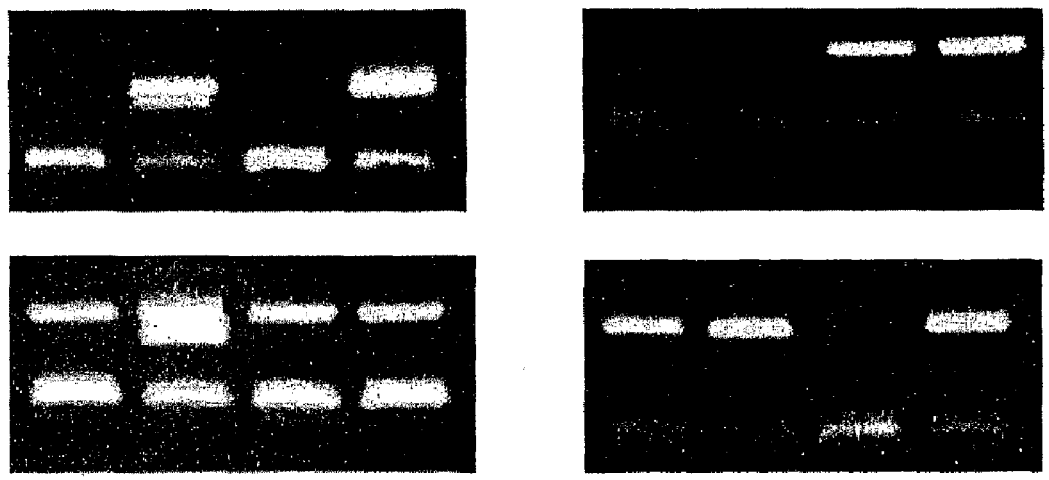
FIG. 2. PCR amplification of cpn60 sequences from individual genomic DNA templates. Templates are environmental bacterial isolates. Templates yielding products of amplification from H1511/H1261 are j0578 (64% G+C), j0580 (63% G+C), j0581 (57% G+C), j0582 (62% G+C), j0583 (55% G+C), j0584 (65% G+C), j0587 (65% G+C), j0588 (57% G+C), j0589 (55% G+C), j0590 (65% G+C) and j0592 (57% G+C). Templates which were not amplified by H1511/H1261 are j0577 (38% G+C), j0579 (G+C content unknown, no sequence available), j0585 (39% G+C), j0586 (G+C content unknown, no sequence available) and j0591

Since initial experiments, we have applied the H1511/H1261 primer set to other bacterial isolates in an attempt to amplify cpn60 sequences from these strains of interest. FIG. 2 shows the results of attempts to amplify cpn60 sequences from a collection of environmental bacterial isolates with a range of G+C contents. The results of this experiment suggest that the primer pair is effective on DNA templates with at least 55% G+C content but ineffective on the templates with <40% G+C.

PCR products generated with H1511/H1261 can be sequenced directly, using H511/H1261 as sequencing primers. However, to obtain the complete sequence of the amplicon would require two sequencing reactions to be conducted since a single sequencing run primed from either side and long enough to span the full length of the amplicon would not include sequence data immediately 3' to the sequencing primer.

For this reason, we also separately pursued H1594/H1595 which include the standard M13(40)F and M13(-48)R sequencing primer landing sights. A single sequencing primed from either of these sites will include the complete sequence of the amplicon.

The H1511/H1261 primer pair would also be useful for generating labeled cpn60 PCR product for use as a probe in hybridization-based identification methods for high G+C templates as described and published previously for the original H279/H280 primer pair. This will enable us to identify microbial species of interest that have high GC content (for example greater than 57% or 58% over the cpn60 universal target as discussed herein) using labeled reference cpn60 amplicon hybridization probes.

Application of H1594/H1595 alone and in cocktails with H729/H730—generation of PCR products from individual template DNAs for direct sequencing.

By themselves, the H1594/H1595 primer pair (and H1511/H1261) so favours high G+C templates that it does not efficiently amplify cpn60 universal target sequences from lower G+C templates. Since we were interested in developing a protocol which would be our first approach for new templates, we created cocktails or mixtures of H1594/H1595 and H729/H730 and tested those molar ratios (10:0, 7:1, 3:1, 1:1, 1:3, 1:7 and 1:10) on the following templates.

c0019 *Brachyspira hyodysenteriae* (32% G+C)

j0481 *Bacillus* sp. (43% G+C)

j0464 *Enterobacter* sp. (53% G+C)

j0495 *Pseudomonas* sp. (59% G+C)

j0438 *Arthrobacter* sp. (60% G+C)

j0508 *Xanthomonas* sp. (63% G+C)

j0381 *Rhodococcus* sp. (64% G+C)

Figure 3:
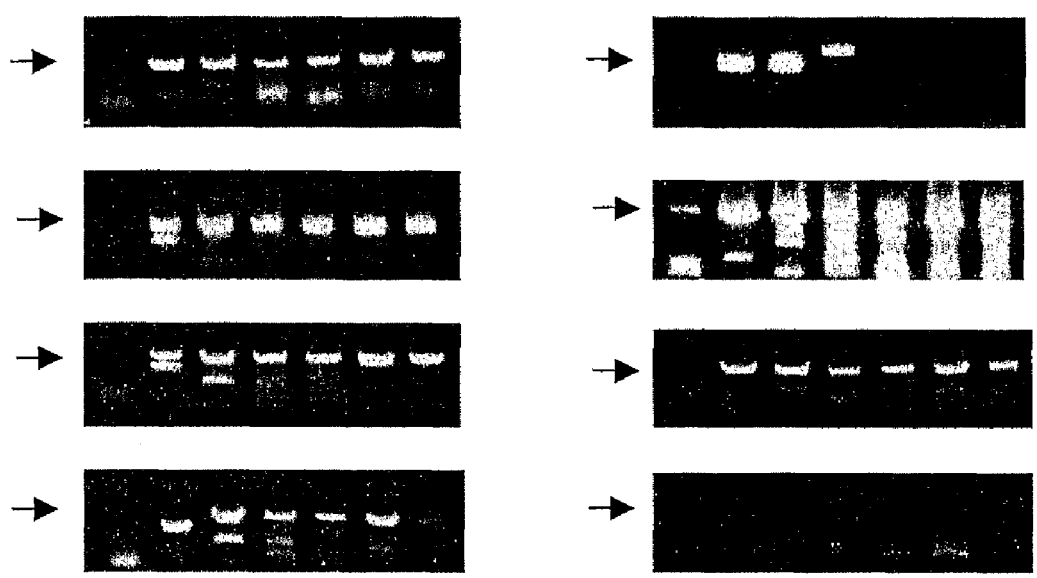
FIG. 3. Agarose gels showing results of PCR reactions using various primer ratios (I=H729+H730; M=H1594+H1595) on templates described fully in the text. Expected PCR product size is ~600 bp (arrow on each gel).

The results of these experiments (FIG. 3) indicated that while amplification occurred to some extent at all ratios, the 3:1 ratio of I:M (H729/H730:H1594/H1595) gave amplification of all templates with little evidence of inappropriate or non-specific amplification products. However, any ratio from 10:1 to 1:10 may be used within the invention.

Since this experiment, we have successfully applied the 3:1 I:M primer cocktail to the amplification of cpn60 universal target sequences from a variety of templates including named reference strains, clinical isolates and environmental isolates.

Environments that we have examined include the microbiota of soils that suppress plant pathogens, the microbiota of the human vagina, the microbiota of activated sludge waste water in pulp and paper mills, the microbiota in intestinal tracts of animals fed control diets or diets that included antimicrobials. Other suitable environments will be apparent to those of skill in the art.

The invention claimed is:

1. A primer pair for amplification of cpn60 targets comprising:
   a first primer consisting of the nucleotide sequence as set forth in SEQ ID NO. 1; and
   a second primer consisting of the nucleotide sequence as set forth in SEQ ID NO. 2.

2. A method of amplifying partial cpn60 sequences from bacterial DNA comprising:
   a) providing a sample comprising bacterial DNA;
   b) adding a primer pair for amplification of bacterial DNA comprising:
      a first primer consisting of the nucleotide sequence as set forth in SEQ ID NO. 1; and
      a second primer consisting of the nucleotide sequence as set forth in SEQ ID NO. 2; and
   c) incubating the sample under conditions suitable for nucleotide amplification.

3. The method according to claim 2 further comprising adding a third primer comprising the nucleotide sequence as set forth in SEQ ID NO. 5 and a fourth primer comprising the nucleotide sequence as set forth in SEQ ID NO. 6 prior to step (c).

4. The method according to claim 3 wherein the first primer and the second primer are added to the sample at a concentration at a ratio of from 1:1 to 10:1 compared to the concentration of the third primer and the fourth primer in the sample.

5. The method according to claim 2 wherein the cpn60 sequences have a G+C content of at least 32%.

6. The method according to claim 2 wherein the cpn60 sequences have a G+C content of 32% to 71%.

* * * * *